(12) United States Patent
Debry et al.

(10) Patent No.: US 8,551,168 B2
(45) Date of Patent: Oct. 8, 2013

(54) VALVE DEVICE INTENDED FOR BEING IMPLANTED IN A DYSFUNCTIONAL LARYNX OR A LARYNX PROSTHESIS

(75) Inventors: Christian Debry, Paris (FR); André Walder, L'Hay les Roses (FR); Roland Duffait, Evans (FR); Sylvain Lefebvre, Vuillafans (FR); Claudia Blank, Stützerbach (DE)

(73) Assignees: Protip SAS, Strasbourg (FR); Universite Louis Pasteur (ULP), Strasbourg (FR); Hopitaux Universitaires de Strasbourg (HUS), Strasbourg (FR)

( * ) Notice: Subject to any disclaimer, the term of this patent is extended or adjusted under 35 U.S.C. 154(b) by 340 days.

(21) Appl. No.: 12/745,462

(22) PCT Filed: Dec. 2, 2008

(86) PCT No.: PCT/FR2008/001667
§ 371 (c)(1),
(2), (4) Date: Oct. 22, 2010

(87) PCT Pub. No.: WO2009/098408
PCT Pub. Date: Aug. 13, 2009

(65) Prior Publication Data
US 2011/0106251 A1    May 5, 2011

(30) Foreign Application Priority Data
Dec. 3, 2007    (FR) .................................... 07 08427

(51) Int. Cl.
*A61F 2/20*        (2006.01)
*A61F 2/04*        (2013.01)

(52) U.S. Cl.
USPC ............................................ 623/9; 623/23.68

(58) Field of Classification Search
CPC ..................................... A61F 2/20; A61F 2/04
USPC ..................... 623/9, 23.68; 604/9; 137/493.1, 137/493.8–493.9, 512.15
See application file for complete search history.

(56) References Cited

U.S. PATENT DOCUMENTS

| 4,374,669 A | 2/1983 | Mac Gregor |
| 4,435,853 A | 3/1984 | Blom et al. |

(Continued)

FOREIGN PATENT DOCUMENTS

| DE | 1 791 014 A1 | 10/1971 |
| DE | 20 2004 010 382 U1 | 12/2004 |

(Continued)

OTHER PUBLICATIONS

International Search Report dated Aug. 5, 2009.

*Primary Examiner* — Andrew Iwamaye
(74) *Attorney, Agent, or Firm* — Buchanan Ingersoll & Rooney PC

(57) ABSTRACT

The present invention relates to a valve device designed to be implanted in a dysfunctional larynx or in a prosthetic larynx. The valve device has a distal portion forming an annular support structure and a central portion forming an obturator. The obturator includes i) a peripheral part forming a first valve integral with the annular support structure in a first hinge region, and ii) a central part forming a second valve integral with the first valve in a second hinge region.

18 Claims, 7 Drawing Sheets

(56) References Cited

U.S. PATENT DOCUMENTS

Figure 1:
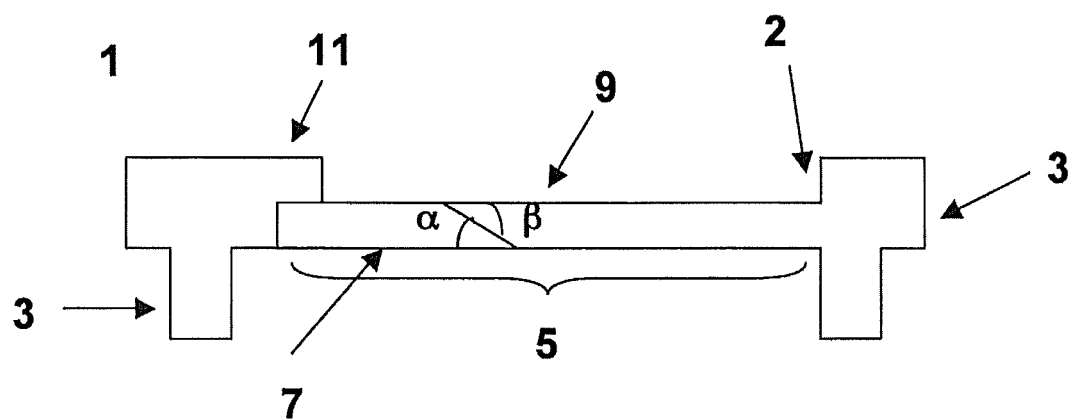

| | | |
|---|---|---|
| 4,538,607 A | 9/1985 | Saul |
| 4,550,448 A | 11/1985 | Kenna |
| 4,614,516 A | 9/1986 | Blom et al. |
| 4,911,716 A | 3/1990 | Blom et al. |
| 5,391,205 A | 2/1995 | Knight |
| 5,507,809 A | 4/1996 | Blom |
| 5,765,560 A | 6/1998 | Verkerke et al. |
| 5,855,612 A | 1/1999 | Ohthuki et al. |
| 5,911,756 A | 6/1999 | Debry |
| 6,358,222 B1 * | 3/2002 | Grundei .......... 604/9 |

FOREIGN PATENT DOCUMENTS

| | | |
|---|---|---|
| EP | 0651 980 A2 | 5/1995 |
| EP | 0 815 807 B1 | 1/1998 |
| EP | 0 856 299 A1 | 8/1998 |
| FR | 2 559 067 A1 | 8/1985 |
| WO | WO 02/066693 | 8/2002 |
| WO | WO 2004/060438 A1 | 7/2004 |

\* cited by examiner

VALVE DEVICE INTENDED FOR BEING IMPLANTED IN A DYSFUNCTIONAL LARYNX OR A LARYNX PROSTHESIS

The present invention relates to the domain of the prosthesis having for function the restoration at the same time of the swallowing, the respiration and the phonation in a patient having suffered, as an example, a total or partial larynx ablation. More particularly, the present invention relates to a valve device intended for being arranged within a prosthesis and whose function consists in allowing the respiration while ensuring the tightness towards other elements such as saliva, mucus or any other element coming from the bolus.

At present time, in France more than 3300 men and 500 women catch annually a larynx cancer. In certain cases, the care require the total ablation of the larynx and the patients loose then the use of the speech, the respiration and the formation of the voice being unable to occur in a natural manner. The respiration is then classically ensured by a definitive tracheotomy.

To recover the ability to talk, different possibilities exist, such as the œsophageal re-education or the use of phonatory prosthesis based on the principle of the tracheoœsophageal fistulae. Such devices are widely described in the prior art and give a certain satisfaction while not being devoid of certain morbidity.

There exist today several types of prosthesis implanted at the level of the tracheoœsophageal wall. As non-limitative examples, we can mention the inventions described in the patent applications U.S. Pat. No. 4,911,716, U.S. Pat. No. 4,614,516, U.S. Pat. No. 4,435,853 or U.S. Pat. No. 5,391,205. Those prosthesis consist of hollow tubes presenting for the majority, at the level of their ends, shoulders or flanges whose function is to maintain the prosthesis in place within the tracheoœsophageal wall, and a valve with a hinge on the œsophagus side, in order to prevent the passage of the fluids from the œsophagus towards the trachea in the respiratory tracts.

The patent application EP 0 651 980 proposes a prosthesis where the invention is based on the implementation of a second backflow preventing valve arranged in the same direction and in series with regards to a first valve.

In the same direction, we can also mention as prior art the patent EP 0 815 807 that describes also a prosthesis intended for curing the dysfunction of the larynx, said prosthesis consisting of a tube presenting at the level of one of its ends conformed in a bevel, on one hand an inclined closing face and on the other hand, lateral openings for communication between the inside and the outside of the tube forming the prosthesis. In practice, the inclined closing face guides the bolus from the mouth to the œsophagus since the lateral openings for communication allow the air circulation in the two directions.

Nevertheless by those can occur leaks and, more particularly, fluids introductions or fluid backflow or of any element of the bolus towards the respiratory tracts. Actually, in practice, the orientation of the closing face is not sufficient to ensure by itself a total tightness.

The present invention aims to cure this disadvantage in proposing a new device allowing on one hand to ensure a perfect tightness of the prosthesis while preventing any leak towards the respiratory tracts and, on the other hand, to allow the air flow in the two directions in order to allow the patient respiration and also the phonation and swallowing functions. Another advantage of the invention, as it will arise further in the description, lies in the fact that the device according to the invention present an excellent wear resistance and therefore has a better life expectancy thus limiting operations of change that remain heavy for the patient.

For this, the present invention proposes a brand new approach that consists in removing the presence of the apertures or of the openings for communication. Actually, the whole devices of the prior art present such openings that allow the air flow necessary to the respiration of the patient. However, these openings being continuously opened, leaks of the bolus or of any other fluid always end up running out in it.

The object of the invention is particularly innovating since it allows, while removing the presence of openings for communication, to ensure the air flow during the inspiration and the expiration, and thus to restore the functions of swallowing, respiration and phonation.

More particularly, the present inventions concerns, in a general manner, a valve device intended for being implanted either within a dysfunctional larynx, or coupled to an artificial larynx prosthesis, said device comprising a distal portion forming an annular support structure and a central portion forming an obturator intended for allowing the air flow and for preventing in an hermetic manner the passage of any other element, said device being characterized in that the obturator comprises i) a peripheral part forming a first valve integral with the annular support structure at the level of a first hinge region, said first valve being able to go down under the effect of the depression resulting from the inspiration by the patient and ii) a central part forming a second valve integral with the first valve at the level of a second hinge region, said second valve being able not only to rise under the effect of the overpressure exerted by the air expired by the patient but also to cooperate with the first valve to go down further to the inspiration by the patient, said first and second valve cooperating with each other in a totally hermetic manner.

In the present description, the expressions "valve", or "obturator" can be used in an interchangeable manner to designate a mobile element able to pass from a closed position to an open position allowing the air flow.

The expressions "distal" and "central" have as a reference the centre of the device according to the invention. From there it follows that the expression "distal portion" makes reference to the portion the more distant from the centre of the device as opposed to the expression "central portion" that makes reference to the closest portion to the centre of said device according to the invention.

According to a preferred embodiment, the circular structure of both valves is preferable owing to the fact that for a given overall dimension, it is this conformation that offers the largest opening for the passage of the air. However such a shape is not restrictive at all and the device according to the invention can have other shapes or structures especially of ovoid section.

Another formulation consists in saying that the invention rests on the cooperation of two valves imbricated one in another in the same plan at rest, the two valves as a whole opening at inspiration when only the smallest opens at expiration.

The functioning of the valves is realized by the overpressure and the depression in the lung during the phases of expiration and inspiration. At inspiration because of the depression existing in the lung the two valves go down in the same movement. At expiration, because of the overpressure existing in the lung only the small valve opens towards the outside of the device, the large valve remaining blocked on its seat. The guarantee of a good tightness of the trachea at the closing of the valves, object of the invention, is a very important element during the swallowing to avoid the food or the saliva to penetrate the trachea then the lungs.

As it will arise from the examples below, one of the characteristics of the invention is based on the thickness of the valves, the latter determining, with the nature of the chosen material, the elasticity of the valve at the level of the hinges regions and thus having an effect directly on its capacity to go down or to maintain its position. This elasticity must be calculated so as to be able to endure the pressure corresponding to the push exerted by the passage of food in the digestive air tracts or to an accumulation of saliva or mucus while being able to go down or to rise following an expiratory overpressure or an inspiratory depression.

In the continuation of the description, the expression "bolus" will be used to define not only any element of said bolus, but also the mucus, the saliva or any other element or foreign body with the respiratory tracts.

According to a preferred embodiment of the invention, the device is characterized in that the annular support structure comprises at least one abutment element preventing the rising of the first valve.

This abutment element plays a key role since it allows to prevent any movement of the first valve towards the top further to the expiration of the patient.

Said abutment element can consist of any means coming to impede and block the movement of the first valve to the top, as for example a pin making a projection of the whole internal circumference of the annular support structure or simply arranged on one or more precise points of said circumference.

According to a preferred embodiment, it is considered that said abutment element consists in that the external circumference of the first valve of the obturator is cut out in the shape of a bevel "to the bottom" and in that the internal circumference of the annular support structure being vis-à-vis is also cut out in the shape of a bevel "inverted to the top", both bevel cuttings cooperating with each other in order to block the rising of the first valve.

The bevel shape is preferred since it allows to ensure a better tightness but any other shape allowing such a cooperation must obviously be considered as equivalent.

This cutting presents, in addition to the advantage of its simplicity, to avoid the adding of an additional piece like a pin, which makes it possible to limit the manufacturing costs and especially to avoid the presence of a piece making a projection and thus suitable for wear and, thereafter, to break leading then the need for an intervention to be able to cure this breaking.

As it was described above, if the first valve is only able to go down under the effect of the depression exerted on its lower face because of the inspiration of the patient, the second valve can, as for it, not only go down in the same manner but also rise under the effect, this time, of the overpressure exerted at the level of its lower face further to the expiration of the patient. It will be easily understood that the first valve undergoes the same overpressure but that, because of the presence of an abutment element, the latter can't rise at all.

With regards to the lowering of the second valve, this one is preferably simultaneous with the lowering of the first valve. According to a preferred form of the invention, it is envisaged a means of cooperation aiming at ensuring this synchronization. More particularly, the first and second valves comprise a cooperation means in order to allow the rising only of the second valve and the simultaneous lowering of the first and second valves.

For the same reasons as those enumerated above with regards to the abutment element, the present invention prefers a cooperation means consisting of that the internal circumference of the first valve is cut out in a bevel "to the bottom" and that the external circumference of the second valve is cut out in a bevel "inverted to the top", the two bevel cuttings cooperating with each other.

Obviously, here also, any means or equivalent element must be considered as encompassed by the scope of the protection conferred by the present patent application. However, the principle of cuttings in a bevel, as considered above, is the only one to ensure a perfect tightness between the two valves.

As is arises from the present description, the two valves are only operated by the effects of depression and overpressure following the respiration of the patient and, on the contrary, must be fixed following another pressure such as the weight of any foreign element which can come, as an example, from the bolus.

The inventors, further to several assays, could determine a thickness of material for the valves, as well as the hinges regions of said valves, that makes it possible to meet those criteria.

This characteristic is completely new in the sense that, for the whole existing devices that are presenting a backflow preventing valve, this valve could only rise following the expiration of the patient and the latter came resting on the end of the prosthesis in order not to subside under the weight of the bolus (the air exchanges occurring, as described above, by openings of communication).

For the first time, it was calculated a thickness of material allowing, by itself, to ensure a sufficient rigidity to be able to resist to the weight of the bolus without going down while ensuring a sufficient elasticity to be able to go down and/or rise under the different air pressures linked to the respiration.

Indeed, as it will arise more precisely from the examples below, the weight of the bolus does not exceed, on average, 7 g, which results in a pressure not exceeding, on average, $0.3 \cdot 10^{-3}$ MPa ou N/mm². The bolus consists of food partially or completely chewed and impregnated with saliva. Further to the swallowing, this bolus will traverse the œsophagus to reach the stomach. Its mass will be diffused following the chewing and the swallowing and according to the nature and the weight of the food which constitutes it, its way in the œsophagus will be more or less fast. In physiological conditions, one can thus reasonably consider that the totality of said bolus will not come to reach a precise point of the device according to the invention at the same moment. Consequently, the pressure of $0.3 \cdot 10^{-3}$ MPa ou N/mm² evoked above is considered as the maximal pressure being able to be exerted on the device. The valve device according to the invention is consequently designed to resist to a pressure lower than the one necessary to support a bolus of 7 g and this is amply sufficient for a good functioning of the valve device.

On the other hand, the overpressure exerted during the expiration of the patient and the depression exerted during the inspiration, being about $10^{-2}$ MPa, that is to say that both are largely higher than the pressure exerted by the bolus, it is easy to understand that the valves will be able to rise or to go down during the respiration of the patient.

More particularly, the device according to the invention is characterized in that the first valve and the first hinge are dimensioned in order to be able to support a load comprised between 0 and 6 g without rising and/or lowering, according to the chosen embodiment.

In the realization of the device according to the invention, it results in the fact that said first and second hinges regions present a thickness comprised between 0.5 and 3.5 mm, preferentially of less than 2.5 mm and more preferentially of 1 mm.

In another embodiment of the invention, it results in the fact that said first and second valve present a thickness comprised between 0.5 and 3.5 mm, preferentially of less than 2.5 mm and more preferentially of 1 mm.

According to an alternative, it can be wished that resistances of the two valves are different in order to be able to adapt, as an example, to patients presenting respiratory problems involving differences of pressures between the inspiration and the expiration. In this precise case, the dimensions of the two valves, as well as the two corresponding hinges regions, can be different.

However, in a general manner, it is preferred that the said first and second valves like the said first and second hinges regions present the same thickness.

This latter embodiment present several advantages like, as an example, the manufacturing costs cutting.

In a preferred embodiment according to the invention, in order to increase the resistance to the pressure exerted by the fluids while not preventing the functioning of the valves, a device of assistance which can be mechanical, electric or electronic is used. Said device of assistance is arranged at the level of the annular support structure and/or at the level of the first valve. The present invention also relates to a valve device for larynx prosthesis where the annular support structure and/or the first valve are provided with a device of assistance which can be mechanical, electric or electronic.

In a particular embodiment, the device of assistance described above is a magnetic device. By magnetic device or magnetic element, it is meant one or more permanent magnets of the lanthanide type which are biocompatible or made biocompatible by various treatments known by one skilled in the art. Preferentially, this or those magnets are chosen from the permanent magnets of the lanthanide type whose remanence is comprised between 1080 and 1150 mT. Said magnetic device can be arranged either on the first valve, or on the internal surface of the support structure of the device according to the invention. On the opposite of this or those magnets when the first valve is in the closed position, we place a metallic element. By metallic element, it is meant one or more metallic elements capable of being magnetic that are arranged in order to enter in contact with the one or more magnets when the first valve is in the closed position. The nature of the magnetic device can be adapted to each situation while making varying the number of magnets and/or their position as an example.

In a particular embodiment, the present invention relates to a valve device for larynx prosthesis comprising a device of assistance that consists of a metallic element arranged at the level of the annular support structure coming in contact with a magnetic element arranged at the level of the first valve.

In a preferred embodiment, the present invention relates to a valve device for larynx prosthesis comprising a device of assistance which consists of a metallic element arranged at the level of the first valve and coming in contact with a magnetic element arranged at the level of the annular support structure.

The magnetic device described above has a mechanical function of assistance of the valve device according to the invention. In a more general manner, it will be easy for one skilled in the art to replace or to complete this magnetic device by any device ensuring an equivalent function or likely to improve this function, such as another device of assistance that can be mechanical, electric or electronic.

Moreover, the hinges regions and the valves can have different thicknesses, those latter being able to be adapted to a precise situation dictated by the state of the patient.

It follows from the invention that, to be able to ensure the elasticity necessary for the good functioning of the valves, at least the hinges regions must be in a semi-rigid material. By "Semi-rigid" it is meant a material that is sufficiently flexible to be able to ensure a certain elasticity while being rigid enough to be able to resist and remain in shape under the effect of a low pressure. In an embodiment, only the hinges regions can be in a semi-rigid material, the valves themselves can be in a rigid material.

However, a preferred embodiment of the invention is that where not only the hinges regions but also the valves are made out in a semi-rigid material that can be identical or different.

According to a more preferred embodiment, the device according to the invention is characterized in that it is completely made up of a semi-rigid material.

Any semi-rigid material, such as defined above, can be used. However, we can cite as a non-limitative example a plastic, a gum, a resin or a silicone. A preferred material consists of silicone 65 Shore A.

According to a preferred embodiment, the device according to the invention is characterized in that said semi-rigid material consists of the silicone.

According to yet a preferred embodiment, the whole device is made out of a semi-rigid material preferentially in silicone. This material present the advantage of being biocompatible and make it possible to avoid, or at least to limit, for example any rejection by the patient.

However, in order to facilitate the support of the device, it can be wished that this one present a certain rigidity at the level of the region ensuring its support, this is to say at the level of the annular support structure.

More particularly, the annular support structure is reinforced by a titanium framework, preferentially in porous titanium.

The titanium presents the advantage of being biocompatible.

Another advantage of the present invention is that said device can be adapted to any type of existing larynx prosthesis.

With this intention, the annular support structure present, at the level of its external circumference, a means forming a removable fixation flange on the larynx prosthesis.

This way, the device according to the invention can be mounted in a removable manner on a larynx prosthesis already installed.

Any removable fixation means can be used but it is however preferred a bayonet system, a "clip" rings system or a system with screws.

Obviously, any equivalent means must be considered as being encompassed by the invention.

Lastly, according to a last aspect of the invention, it is also aimed a larynx prosthesis including, assembled removable as seen above or directly integrated within it, a device according to the invention. The present application describes the use of a device according to the invention within an artificial larynx prosthesis. More particularly, said device is positioned at the level of the upper end of said prosthesis. The invention concerns an artificial larynx prosthesis comprising, at the level of its upper portion, a device according to the invention such as described above.

According to a preferred embodiment, the artificial prosthesis is characterized in that said device according to the invention is arranged perpendicularly to the longitudinal axis of the prosthesis.

According to a second embodiment, whose realization will arise clearly from the examples below, the device according to the invention is arranged inclined in comparison with the longitudinal axis of the prosthesis according to an angle comprised between 0 and 60 degrees.

Figure 2:
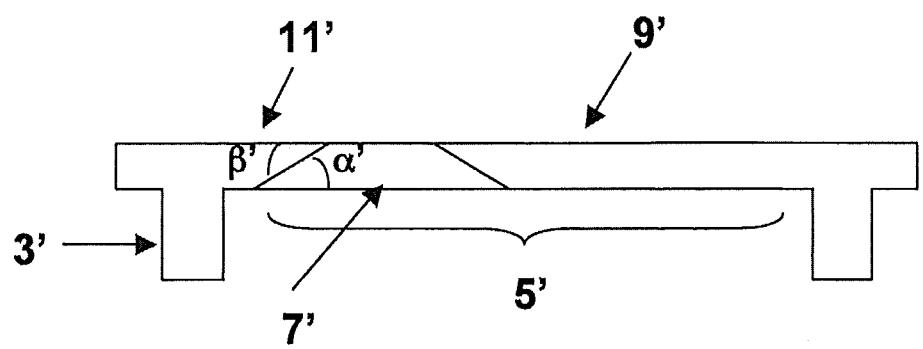
Figure 3:
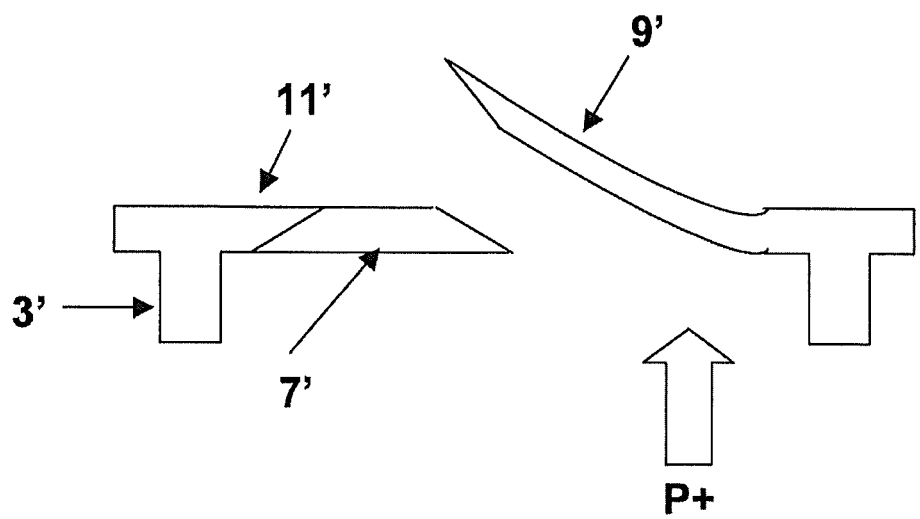
Figure 4:
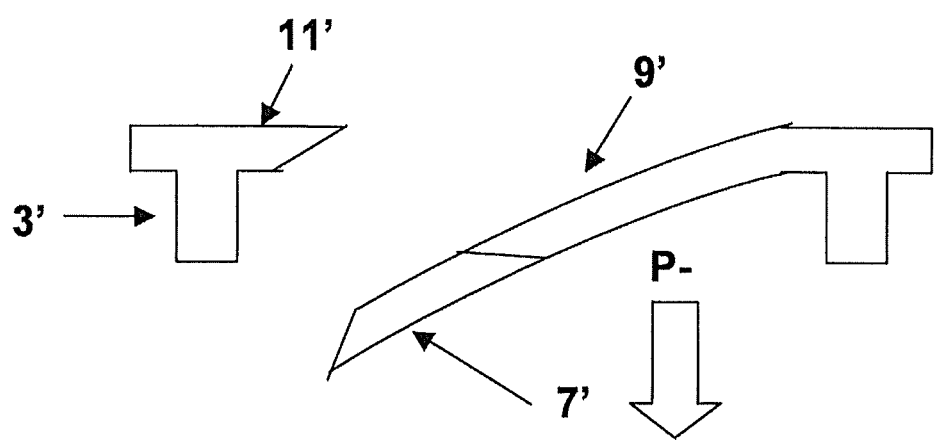
Figure 5:
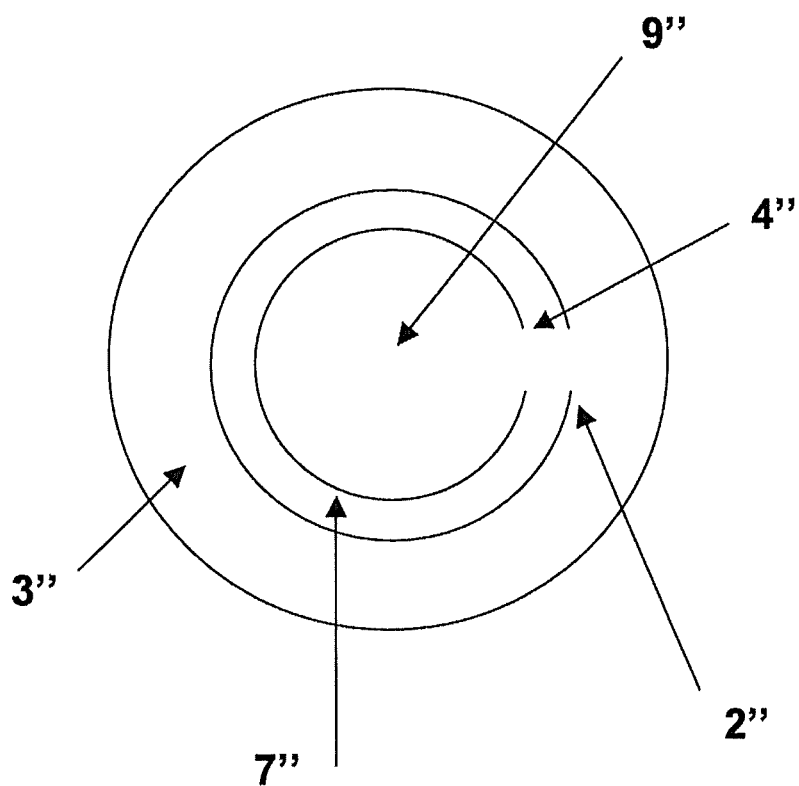
Figure 6:
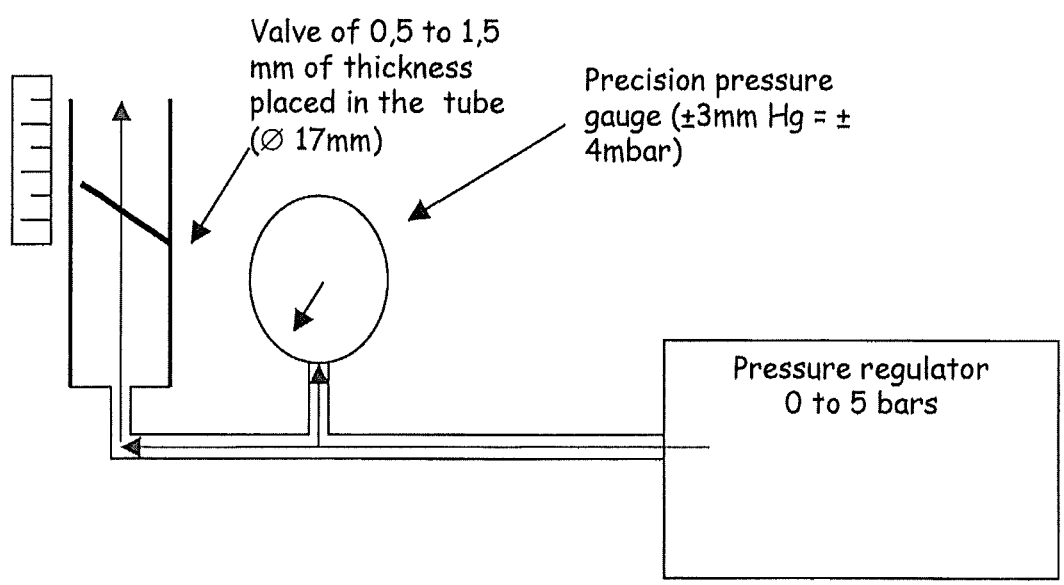
Figure 7:
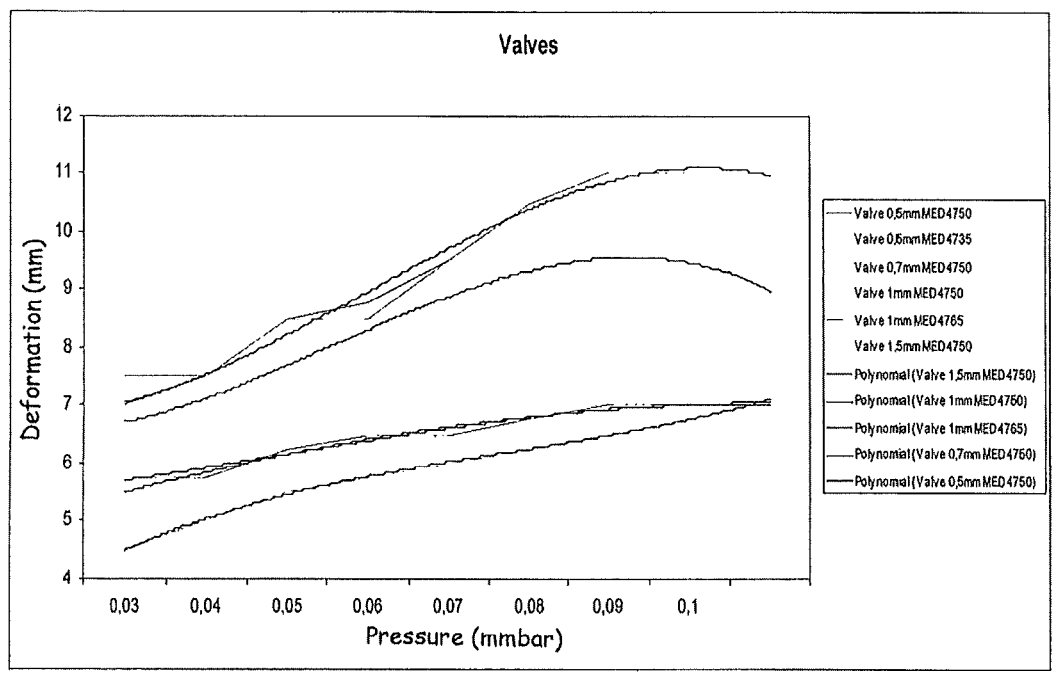
Figure 8:
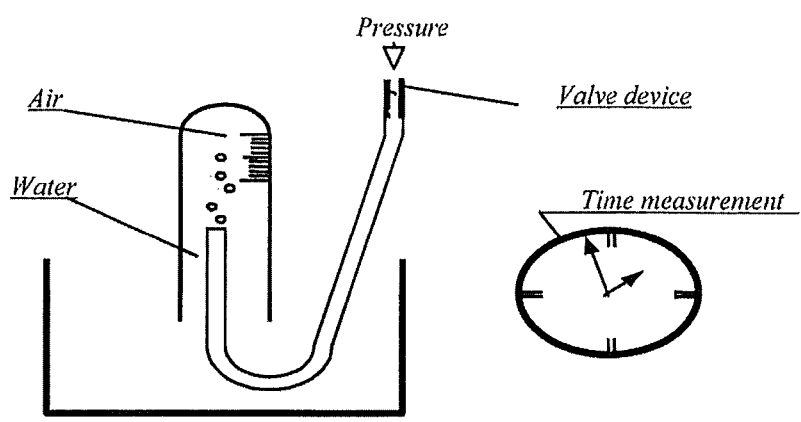
Figure 9:
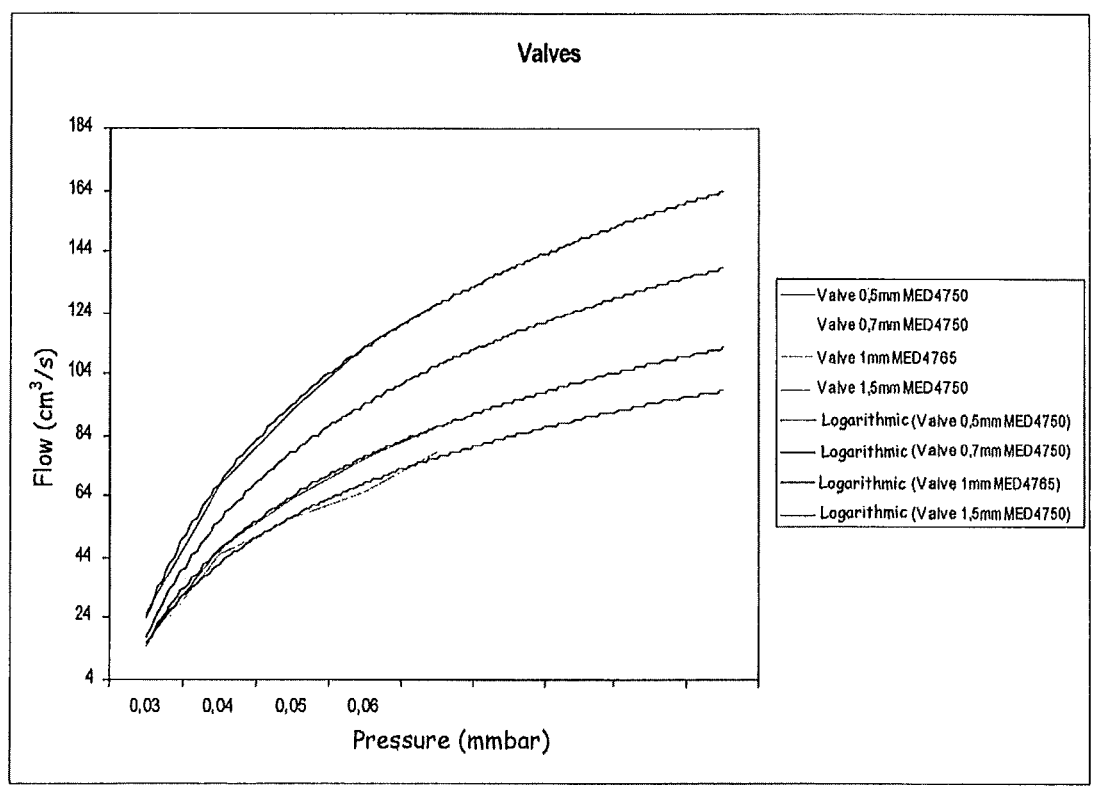
Figure 10:
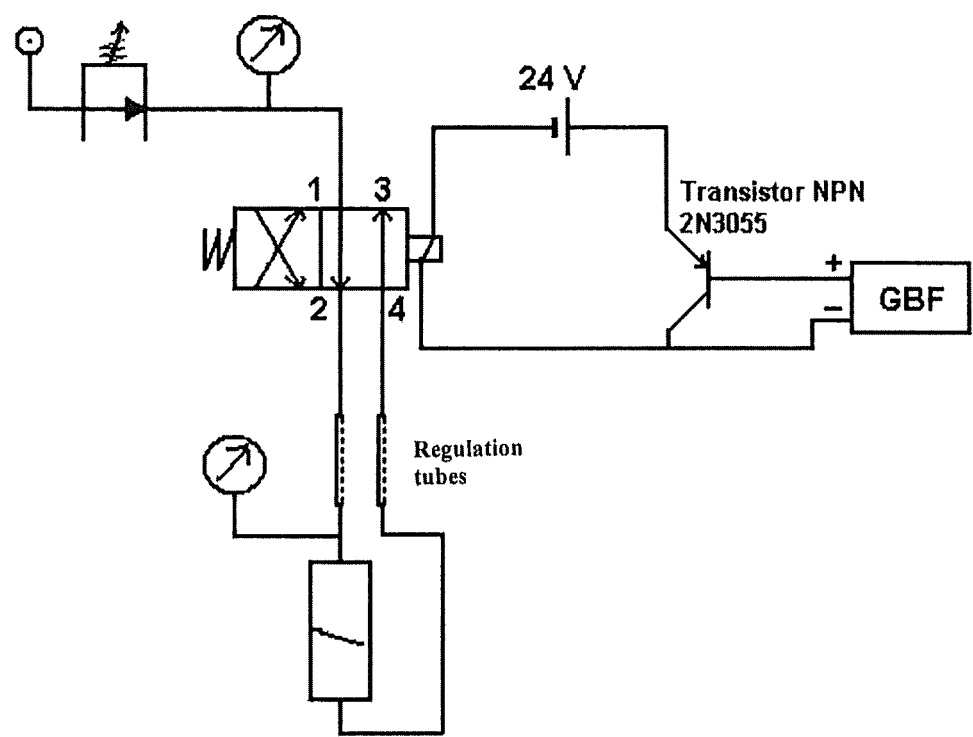

The invention will be better understood in the light of the examples below as well as the following figures, in which:

The FIG. 1 represents, seen in cross section, a first embodiment of a device according to the invention, The FIG. 2 represents, seen in cross section, a second embodiment of a device according to the invention, The FIG. 3 represents the device according to the invention of the FIG. 2 in the expiration phase of the patient, The FIG. 4 represents the device according to the invention of the FIG. 2 in the inspiration phase of the patient, The FIG. 5 represents a view from the top of the device according to the invention, The FIG. 6 represents a plan of the assembly for the measurement of the deformation in function of the pressure, The FIG. 7 represents, in a graphic manner, the results obtained by the measurement of the deformation, The FIG. 8 represents the plan of the assembly for the measurement of the air flow, The FIG. 9 represents, in a graphic manner, the results obtained for the measurement of the air flow, The FIG. 10 represents a plan of the assembly realized for the measurement of the effort test.

EXAMPLES

If one refers to FIG. 1, it is represented a device 1 according to the invention out of a longitudinal section. The device comprises an annular support structure 3 corresponding to the largest external circumference of the device 1. As represented on this figure, said support structure presents, out of cut, a T shape, the vertical bar of the T coming to fit into the prosthesis whereas the eternal end of the horizontal bar comes to take support on the upper end of the prosthesis preventing thereby the device 1 to move and to be inserted within the larynx prosthesis. Obviously, such a T shape is not at all limitative and any shape ensuring the same function must be regarded as equivalent.

On this same FIG. 1, the central portion forming obturator 5 is well visible at the centre and comprises a first valve 7 and a second valve 9, said first and second valves 7 and 9 being solid with the annular support structure 3 at the level respectively of the hinges regions 2 and 4 (on this figure, for clearness preoccupations, only the hinge region 2 could be represented, the two hinges regions appearing clearly on the FIG. 5). This figure being a cut made at the level of the hinges regions 2 and 4, it must be understood that the first valve 7 makes the turn of the second valve 9 except for the hinges regions 2 and 4. This last point will arise more clearly from the FIG. 5 which represents the device 1 seen from the top. On this FIG. 1 is shown an abutment element 11 under the shape of a pin making a projection from the annular support structure 3 towards the inside in order to come blocking any movement of the first valve 7 to the top. This element 11, represented also here out of cut can be present on the whole internal circumference of the support structure 3 or only punctually.

This FIG. 1 also clearly highlights the nature of the cooperation means between the first valve 7 and the second valve 9. More particularly, the internal or central circumference of the first valve 7 is cut out in the shape of a bevel "to the bottom", that is to say that the upper surface of said first valve 7 is shorter than the lower surface resulting thus in a bevel forming an angle $\alpha$ strictly comprised between 90 and 180°. On the other hand, the external or distal circumference of the second valve 9 is also cut out in a bevel, but the bevel is "inverted to the top", that is to say that the upper surface of said second valve 9 is, this time, longer than the lower surface thus resulting in a cutting in a bevel of an angle $\beta$ strictly comprised between 0 and 90°. Of course, for a good cooperation of the first and second valves 7 and 9, the sum of the two angles $\alpha$ and $\beta$ must be equal to 180°, which is equivalent to say that said two angles $\alpha$ and $\beta$ are complementary.

The FIG. 2 represents another embodiment of the invention in which the abutment element 11' making a projection from the annular support structure 3' is replaced by a particular cutting in bevel. More particularly, the external or distal circumference of the first valve 7' is cut out in a bevel "to the bottom", that is to say that the upper surface of said external or distal circumference is shorter than the lower surface so as to form a bevel where the angle $\alpha'$ is strictly comprised between 90 and 180°. On the other hand, the internal or central circumference of the annular support structure 3' is, as for it, cut out in a bevel "inverted to the top", that is to say that the upper surface of this internal or central circumference is longer than the lower surface so as to form also a bevel whose angle $\beta'$ is, in this case, comprised strictly between 0 and 90°. In a similar manner to the cooperation means between the first and second valves 7 and 9 described above, the sum of the angles $\alpha'$ and $\beta'$ must be equal to 180°.

The FIG. 3 represents the device according to the invention described above at the expiration of the patient. On this figure, it arises clearly that only the second valve 9' is able to rise under the effect of the overpressure $P^+$ exerted by the rejection of air by the patient during the expiration, overpressure that comes to push the whole made of by the two valves 7' and 9', said first valve 7' being as for him unable to rise because of the cutting in a bevel forming an abutment element 11'.

The FIG. 4 represents the same device in the phase of inspiration during which a depression $P^-$ occurs at the level of the lower surfaces respectively of the first and second valves 7' and 9', this depression resulting in the lowering of said first and second valves 7' and 9', the first valve 7' falling simultaneously with the second valve 9' due to the fact that the cutting in a bevel forms a cooperation means.

As described above, the FIG. 5 represents a view from the top of the device according to the invention. Il arises from this figure that the whole device, that is to say the annular support structure 3", the first valve 7" and the second valve 9" present a circular shape. Such a circular shape is not limitative at all and any other shape can be considered such as ovoid shapes, square, star, etc.

This figure shows the annular support structure 3" then, forming a smaller circle than the first valve 7" and, forming an even smaller circle, the second valve 9". The first valve 7" is integral with the annular support structure 3" at the level of a hinge region 2" whereas the second valve 9" is integral with, as for it, the first valve at the level of the hinge region 4". The hinge region 4" being in the prolongation of the hinge region 2", it appears thus that the second valve 9", like the first valve 7", are both integral with, directly or indirectly, the annular support structure 3".

The examples below allow to illustrate some characteristics of the invention that were highlighted by the inventors.

Example 1

Measurement of Deformation and of Air Flow a. Measurement of Deformation

In this part, the deformation of the valve made of silicone for different values of pressure exerted on it was measured.

The plan of assembly for the measurement of the deformation in function of the pressure is represented at FIG. 6.

The results obtained are gathered in table 1 below.

TABLE 1

| Pressure (bar) | Pressure (mmHg) | Valve 0.5 mm MED 4750 (mm) | Valve 0.5 mm MED 4735 (mm) | Valve 0.7 mm MED 4750 (mm) | Valve 1 mm MED 4750 (mm) | Valve 1 mm MED 4765 (mm) | Valve 1.5 mm MED 4750 (mm) |
|---|---|---|---|---|---|---|---|
| 0.03 | 22.5 | 7 | 7.5 | 6.75 | 5.5 | 5.75 | 4.5 |
| 0.04 | 30 | 7.5 | 7.5 | 7 | 5.75 | 5.75 | 5 |
| 0.05 | 37.5 | 8.5 | 8.5 | 7.75 | 6.25 | 6.25 | 5.5 |
| 0.06 | 45 | 8.75 | 8.5 | 8.25 | 6.5 | 6.5 | 5.75 |
| 0.07 | 52.5 | 9.5 | 9.5 | 9 | 6.5 | 6.5 | 6 |
| 0.08 | 60 | 10.5 | 10.5 | 9.25 | 6.75 | 6.75 | 6.25 |
| 0.09 | 67.5 | 11 | 11 | 9.5 | 7 | 7 | 6.5 |
| 0.1 | 75 | 11 | 11 | 9.5 | 7 | 7 | 6.75 |

The representation of the results under the form of a diagram is shown on FIG. 7.

For the valve of 0.5 mm:
At the time of the setting under pressure, we can observe a rapid deformation of the valve, which results in a passage of air relatively important.
When we inspire and we expire inside the tube, we note no difficulty.
Some frictions are noted at the level of the valve and the tube, with high pressure (>0.3 bar), causing a deformation of the sides of the valve.

For the valve of 0.7 mm:
The deformation of the valve is a bit smaller than for the valve of 0.5. The passage of the air is always as well ensured.
At the time of a series of inspiration and expiration, we note no difficulty.
The same frictions as for the valve of 0.5 are recorded.

For the valve of 1 mm:
We record a deformation smaller than for the preceding valves while ensuring a correct passage of air.
The respiration is made without any effort to provide.
The same frictions as for the valve of 0.7 are recorded.

For the valve of 1.5 mm:
Idem than for the preceding valve.

From the curves, we will note a saturation effect due in particular to the frictions from the sides of the valve on the walls of the tube. This effect is relatively reduced for the valves of 1 mm and 1.5 mm because those become less deformed, however the valve of 1 mm remains the most suitable. The hardness has practically no notable effect on the measurements.

b. Measurement of the Air Flow

The air flow was measured by the volume of air stored during a given period of time in a graduated test tube filled with water, turned over on a tank also containing water.
The plan of assembly is represented on FIG. 8.
The results obtained are represented in table 2 below.

TABLE 2

| Pressure (bar) | Pressure (mmHg) | Valve 0.5 mm MED 4750 (cm3/s) | Valve 0.7 mm MED 4750 (cm3/s) | Valve 1 mm MED 4765 (cm3/s) | Valve 1.5 mm MED 4750 (cm3/s) |
|---|---|---|---|---|---|
| 0.03 | 22.5 | 25 | 20 | 15.43 | 14.88 |
| 0.04 | 30 | 68 | 52.08 | 47.16 | 44.64 |
| 0.05 | 37.5 | 92.3 | 79.42 | 63.2 | 56.8 |
| 0.06 | 45 | 113.1 | 92.6 | 76.52 | 65.7 |
| 0.07 | 52.5 | 127.2 | 108.8 | 86.9 | 77.9 |

The results under a graphic form are also represented on FIG. 9.

We notice a very slight saturation of the value of the flow for the high values of air pressure, which corresponds to the abutment of the membrane on the wall, noticed previously in the measurement of the deformation.

Example 2

Effort Test

Those effort tests have as an objective to study the behaviour and the deformations of the valve after two million of cycles of respiration, which corresponds to a three months functioning.
The plan of assembly is represented on FIG. 10.
The tests were followed until 20 million of cycles (more than 900 days of real functioning), with fold in the two directions under an alternate pressure of 22 mm of Hg, that is to say 30 mbar, at a frequency of 10 Hz; no deformation of the membrane appeared; only the hinge zone is apparent.
The theoretical analyses are in conformity with the results of the experimental tests carried out.
In comparison with these results, we can thus give the valve of 1 mm as the more appropriate for the realization of a valve for a larynx prosthesis.
The siliconed material used during the tests is biocompatible.

Example 3

Larynx Prosthesis Provided with a Valve Device Equipped with a Mechanical Device of Assistance This mode of realization consists in a valve device according to the invention in which a magnetic device is added to increase the resistance to the pressure of said valve system. This valve system is arranged on a larynx prosthesis provided with a massive titanium ring that will come to reinforce the prosthesis in its distal part, at the internal level.

A. Magnetic Device: One Magnet

The magnetic device consists of a magnet Neo-Delta Neodymium-iron-boron (NdFeB) having a parallelepipedic form and having the dimensions 2 mm×2 mm×1 mm (reference NE22, commercialized by Binder Magnetic®). This magnet presents the advantage of being very strong for a small size. It is also made perfectly biocompatible by an anticorrosion treatment. This magnet is positioned on the first valve in silicone, at the opposite of the hinge region.

The support structure is reinforced at the level of its internal surface by a massive titanium ring. This ring will support a metallic element capable of being magnetic and positioned so as to be able to enter in contact with the magnet when the first valve is in the closed position.

B. Magnetic Device: Two Magnets

The magnetic device consists of two magnets Neo-Delta Neodymium-iron-boron (NdFeB) having a parallelepipedic form and having the dimensions 2 mm×2 mm×1 mm (reference NE22, commercialized by Binder Magnetic®). Those magnets are arranged on the first valve in silicone on each side of a vertical joining the hinge region to its opposite. Those magnets can be positioned with variable distances from this vertical.

The support ring is provided with two metallic elements capable of being magnetic and positioned so as to be able to enter in contact with the magnets when the first valve is in the closed position.

Example 4

Larynx Prosthesis Provided with a Valve Device Equipped with a Mechanical Device of Assistance This embodiment consists of a valve device according to the invention in which a magnetic device is added in order to increase the resistance to the pressure of said valve system. This valve system is arranged on a larynx prosthesis provided with a massive titanium ring that will come to reinforce the prosthesis in its distal part, at the internal level.

A. Magnetic Device: One Magnet

The magnetic device consists of one magnet Neo-Delta Neodymium-iron-boron (NdFeB) having a parallelepipedic form and having the dimensions 2 mm×2 mm×1 mm (reference NE22, commercialized by Binder Magnetic®). This magnet presents the advantage of being very strong for a small size. It is also made perfectly biocompatible with an anticorrosion treatment.

The magnet is arranged on the support structure on the opposite to the hinge region of the valves.

The first valve is provided with a metallic element suitable for being magnetic, arranged in such a manner that it can enter in contact with the magnet when the first valve is in closed position.

B. Magnetic Device: Three Magnets

The magnetic device consists of three magnets Neo-Delta Neodymium-iron-boron (NdFeB) having a parallelepipedic form and having the dimensions 2 mm×2 mm×1 mm (reference NE22, commercialized by Binder Magnetic®). These magnets are arranged on the reinforcement ring of the support structure and positioned in three different points:

- at the opposite from the hinge region
- on both sides of a vertical joining the hinge region to its opposite; this two magnets can be positioned with variable distances from this vertical. The first valve is provided with three metallic elements likely to be magnetic and arranged in order come in contact with the magnets when the first valve is in closed position.

In a general manner, the present description aims to illustrate the invention in the clearer manner and any change in the realization must be considered as equivalent and, thereby, being encompassed by the following claims that define the scope of the desired protection.

The invention claimed is:

1. Valve device intended for being implanted in a dysfunctional larynx or in an artificial prosthetic larynx, said valve device comprising a distal portion forming an annular support structure and a central portion forming an obturator intended for allowing air flow and for preventing passage of any other element, wherein said obturator comprises:
   i) a peripheral part forming a first valve integral with the annular support structure at a level of a first hinge region, said first valve being able to go down under an effect of a depression resulting from an inspiration by a patient; and
   ii) a central part forming a second valve integral with the first valve at a level of a second hinge region, said second valve being able to rise under an effect of an overpressure exerted by air expired by the patient and said second valve also being able to cooperate with the first valve to depress further to the inspiration by the patient, said first and second valve cooperating with each other in a totally hermetic manner;
   wherein the first and second valves comprise a cooperating means in order to allow rising only of the second valve and simultaneous lowering of the first and second valves.

2. The valve device according to claim 1, wherein the annular support structure comprises at least one abutment element preventing a rising of the first valve.

3. The valve device according to claim 2, wherein said abutment element is defined by an external circumference of the first valve of the obturator being cut a bevel to the bottom and an internal circumference of the annular support structure being cut at a bevel inverted to the top, whereby the bevel cuttings of the first valve and the annular support structure cooperate with each other in order to block the rising of the first valve.

4. The valve device according to claim 1, wherein said cooperating means is defined by an internal circumference of the first valve being cut at a bevel "to the bottom" and an external circumference of the second valve being cut at a bevel "inverted to the top", whereby the bevel cuttings of the first valve and the second valve cooperate with each other.

5. The valve device according to claim 1, wherein said first and second hinge region present a thickness comprised between 0.5 and 3.5 mm.

6. The valve device according to claim 5, wherein said first and second valve present a thickness comprised between 0.5 and 3.5 mm.

7. The valve device according to claim 5, wherein said first and second valve and said first and second hinge region present the same thickness.

8. The valve device according to claim 1, wherein it is entirely consisting of a semi-rigid material.

9. The valve device according to claim 8, wherein said semi-rigid material consists of silicone.

10. The valve device according to claim 8, wherein the annular support structure is reinforced by a titanium frame.

11. The valve device according to claim 1, wherein the annular support structure presents, at a level of its external circumference, means forming a removable fixation flange for mounting on the dysfunctional larynx or the artificial prosthetic larynx.

12. The valve device according to claim 11, wherein said removable fixation flange consists of a bayonet system, a rings system or a screw system.

13. The valve device according to claim 1, wherein at least one of the annular support structure and the first valve is provided with an assisting device being able to be mechanical, electric or electronic.

14. The valve device according to claim 13, wherein said assistance device consists of a metallic element arranged at a level of the annular support structure coming in contact with a magnetic element arranged at a level of the first valve.

15. The valve device according to claim 13, wherein said assistance device consists of a metallic element arranged at a level of the first valve coming in contact with a magnetic element arranged at a level of the annular support structure.

16. Artificial larynx prosthesis comprising, at a level of its upper portion, a device according to claim 1.

17. Artificial larynx prosthesis according to claim 16, wherein said device is arranged perpendicularly to a longitudinal axis of the prosthesis.

18. Artificial prosthesis according to claim 16, wherein said device is arranged inclined in comparison with a longitudinal axis of the prosthesis according to an angle comprised between 0 and 60 degrees.

* * * * *